US011357862B2

United States Patent
Wu et al.

(10) Patent No.: US 11,357,862 B2
(45) Date of Patent: Jun. 14, 2022

(54) PEPTIDE-CONJUGATED NANOPARTICLES FOR TARGETING, IMAGING, AND TREATMENT OF PROSTATE CANCER

(71) Applicant: Academia Sinica, Taipei (TW)

(72) Inventors: Han-Chung Wu, Taipei (TW); Chen-Yun Yeh, Keelung (TW)

(73) Assignee: Academia Sinica, Taipei (TW)

( * ) Notice: Subject to any disclaimer, the term of this patent is extended or adjusted under 35 U.S.C. 154(b) by 1036 days.

(21) Appl. No.: 16/062,274

(22) PCT Filed: Jan. 11, 2017

(86) PCT No.: PCT/US2017/012962
§ 371 (c)(1),
(2) Date: Jun. 14, 2018

(87) PCT Pub. No.: WO2017/123600
PCT Pub. Date: Jul. 20, 2017

(65) Prior Publication Data
US 2021/0236647 A1    Aug. 5, 2021

Related U.S. Application Data

(60) Provisional application No. 62/278,295, filed on Jan. 13, 2016.

(51) Int. Cl.
| | |
|---|---|
| *A61K 47/62* | (2017.01) |
| *A61K 47/69* | (2017.01) |
| *A61K 47/66* | (2017.01) |
| *A61P 35/00* | (2006.01) |
| *A61K 9/127* | (2006.01) |
| *A61K 49/00* | (2006.01) |
| *A61K 49/18* | (2006.01) |
| *C07K 7/08* | (2006.01) |
| *A61K 47/64* | (2017.01) |

(52) U.S. Cl.
CPC ............ *A61K 47/62* (2017.08); *A61K 9/1271* (2013.01); *A61K 47/64* (2017.08); *A61K 47/66* (2017.08); *A61K 47/665* (2017.08); *A61K 47/6911* (2017.08); *A61K 49/0084* (2013.01); *A61K 49/1866* (2013.01); *A61P 35/00* (2018.01); *C07K 7/08* (2013.01)

(58) Field of Classification Search
None
See application file for complete search history.

(56) References Cited

PUBLICATIONS

New England Biolabs, Ph.D.TM Phage Display Libraries, Instruction Manual, version 1.1, published Oct. 2012 (Year: 2012).*
International Search Report for PCT/US2017/012962, dated Apr. 4, 2017.
Written Opinion of International Search Authority for PCT/US2017/012962, dated Apr. 4, 2017.
Chen-Yun Yeh et al. "Peptide-conjugated nanoparticles for targeted imaging and therapy of prostate cancer" Biomaterials 99 (2016) 1-15.

* cited by examiner

*Primary Examiner* — Christina Bradley
(74) *Attorney, Agent, or Firm* — Hsiu-Ming Saunders; Intellectual Property Connections, Inc.

(57) ABSTRACT

An isolated or a synthetic targeting peptide comprising an amino acid sequence that is at least 90% identical to SEQ ID NO: 8 is disclosed. The targeting peptide may be conjugated to a component selected from the group consisting of polymeric micelles, lipoprotein-based drug carriers, nanoparticle drug carriers, a chemotherapeutic agent, a micelle, a liposome, dendrimers, a polymer, a lipid, an oligonucleotide, a peptide, a polypeptide, a protein, a prostate cancer cell, a stem cell, and an imaging agent. Also disclosed are a kit for imaging and detecting the presence of prostate cancer cells in vivo or in vitro, and a composition for treating prostate cancer, inhibiting prostate cancer cell growth, inducing prostate cancer cell cytotoxicity, and/or increasing the survival rate in a prostate cancer patient.

19 Claims, 7 Drawing Sheets
Specification includes a Sequence Listing.

PEPTIDE-CONJUGATED NANOPARTICLES FOR TARGETING, IMAGING, AND TREATMENT OF PROSTATE CANCER

REFERENCE TO RELATED APPLICATION

This application is a national stage application (under 35 U.S.C. 371) of PCT/US2017/012962 filed on 11 Jan. 2017, which claims priority to US provisional application 62/278,295 filed on 13 Jan. 2016, all of which are herein incorporated by reference in their entireties.

FIELD OF THE INVENTION

The present invention relates generally to a drug delivery system, and more specifically to a prostate cancer targeted drug delivery system.

BACKGROUND OF THE INVENTION

Prostate cancer is the most common male malignancy and the second leading cause of cancer death among men in developed countries. Patients of early stage prostate cancer are treated with prostatectomy, radiotherapy, and/or brachytherapy. Patients of advanced stage prostate cancer are subjected to androgen deprivation therapy, which specifically targets androgen receptor in localized prostate cancer.

Castration-resistant prostate cancer patients are usually treated with chemotherapeutic agents, including docetaxel. In addition, abiraterone acetate and enzalutamide, both of which decrease androgen receptor signaling, are also beneficial to survival. Chemotherapeutic agents encapsulated within ligand-targeted nanoparticles can have increased therapeutic efficacy against tumors. Active tumor-targeting drug delivery can be achieved through various targeting molecules, such as antibodies, peptides, or aptamers.

Peptide phage display technology is a powerful tool for identification of disease-specific antigens that recognize tumor targets. Screening phage display libraries against specific target tissues is therefore a fast and direct method for identifying peptide sequences that might be suitable for drug targeting.

SUMMARY OF THE INVENTION

In one aspect, the invention relates to a conjugate comprising:
(a) an isolated or a synthetic targeting peptide comprising an amino acid sequence that is at least 90% identical to SEQ ID NO: 8; and
(b) a component, to which the targeting peptide is conjugated, the component being selected from the group consisting of polymeric micelles, lipoprotein-based drug carriers, nanoparticle drug carriers, a chemotherapeutic agent, a micelle, a liposome, dendrimers, a polymer, a lipid, an oligonucleotide, a peptide, a polypeptide, a protein, a prostate cancer cell, a stem cell, and an imaging agent.

In one embodiment, the targeting peptide is conjugated to: (a) the chemotherapeutic agent; (b) the oligonucleotide; (c) the imaging agent; or (d) the liposome. In another embodiment, the component is the liposome and the conjugate further comprises one or more anti-cancer agents encapsulated within the liposome. In another embodiment, the targeting peptide consists of less than 20 amino acid residues in length. In another embodiment, the liposome is PEGylated. In another embodiment, the imaging agent is selected from the group consisting of quantum dots, superparamagnetic iron oxide nanoparticles, and a fluorescent dye encapsulated within a liposome.

In another aspect, the invention relates to use of a conjugate of the invention in the manufacture of a medicament or a kit for imaging and detecting the presence of prostate cancer cells in vivo or in vitro.

The invention also relates to a conjugate of the invention for use in imaging and detecting the presence of prostate cancer cells in vivo or in vitro. Alternatively, the invention relates to a method of detecting the presence of prostate cancer cells in vivo or in vitro, comprising: (a) providing the conjugate of the invention; (b) causing the prostate cancer cells to be exposed to the conjugate in vitro or in vivo; (c) allowing the targeting peptide of the conjugate to bind to the prostate cancer cells in vitro or in vivo; and (d) performing imaging to detect the presence of the prostate cancer cells in vitro or in vivo.

Further in another aspect, the invention relates to a kit for imaging and detecting the presence of prostate cancer cells in vivo or in vitro, comprising: (a) the conjugate of the invention; and (b) a written instruction for use of the kit in imaging and detecting the presence of prostate cancer cells.

In another aspect, the invention relates to an isolated or a synthetic targeting peptide comprising an amino acid sequence that is at least 90% identical to SEQ ID NO: 8. In one embodiment, the targeting peptide comprises the amino acid sequence of SEQ ID NO: 8. In another embodiment, the targeting peptide consists of less than 20 amino acid residues in length. In another embodiment, the targeting peptide is conjugated to a liposome, a PEGylated liposome, a nanoparticle, or an imaging agent.

Further in another aspect, the invention relates to a composition comprising: (a) liposomes; (b) a therapeutically effective amount of one or more chemotherapeutic agents, encapsulated within the liposomes; and (c) an isolated or a synthetic targeting peptide comprising an amino acid sequence that is at least 90% identical to SEQ ID NO: 8, being conjugated to the surfaces of the liposomes. In one embodiment, the composition comprises two or more different chemotherapeutic agents with each chemotherapeutic agent being separately encapsulated within the liposomes.

Yet in another aspect, the invention relates to use of a composition of the invention in the manufacture of a medicament for treating prostate cancer, inhibiting prostate cancer cell growth, inducing prostate cancer cell cytotoxicity, and/or increasing the survival rate in a prostate cancer patient. Alternatively, the invention relates to a composition of the invention for use in treating prostate cancer, inhibiting prostate cancer cell growth, inducing prostate cancer cell cytotoxicity, and/or increasing the survival rate in a prostate cancer patient.

(E) Prussian blue staining of PC3 xenografts in mice injected with SPIONs or SP204-SPIONs. Two groups of SCID mice bearing PC3 xenografts were subjected to 7 Tesla MRI analysis after tail vein injection of SPIONs (F) or SP204-SPIONs (G) for 4 hours. MRI images were taken before and after injection (n=3). (H) Histogram analysis of MR signal intensity in the SP204-SPION-treated group revealed a 20.1% lower signal intensity than that in the xenograf group. *, p<0.05.

Figure 5:
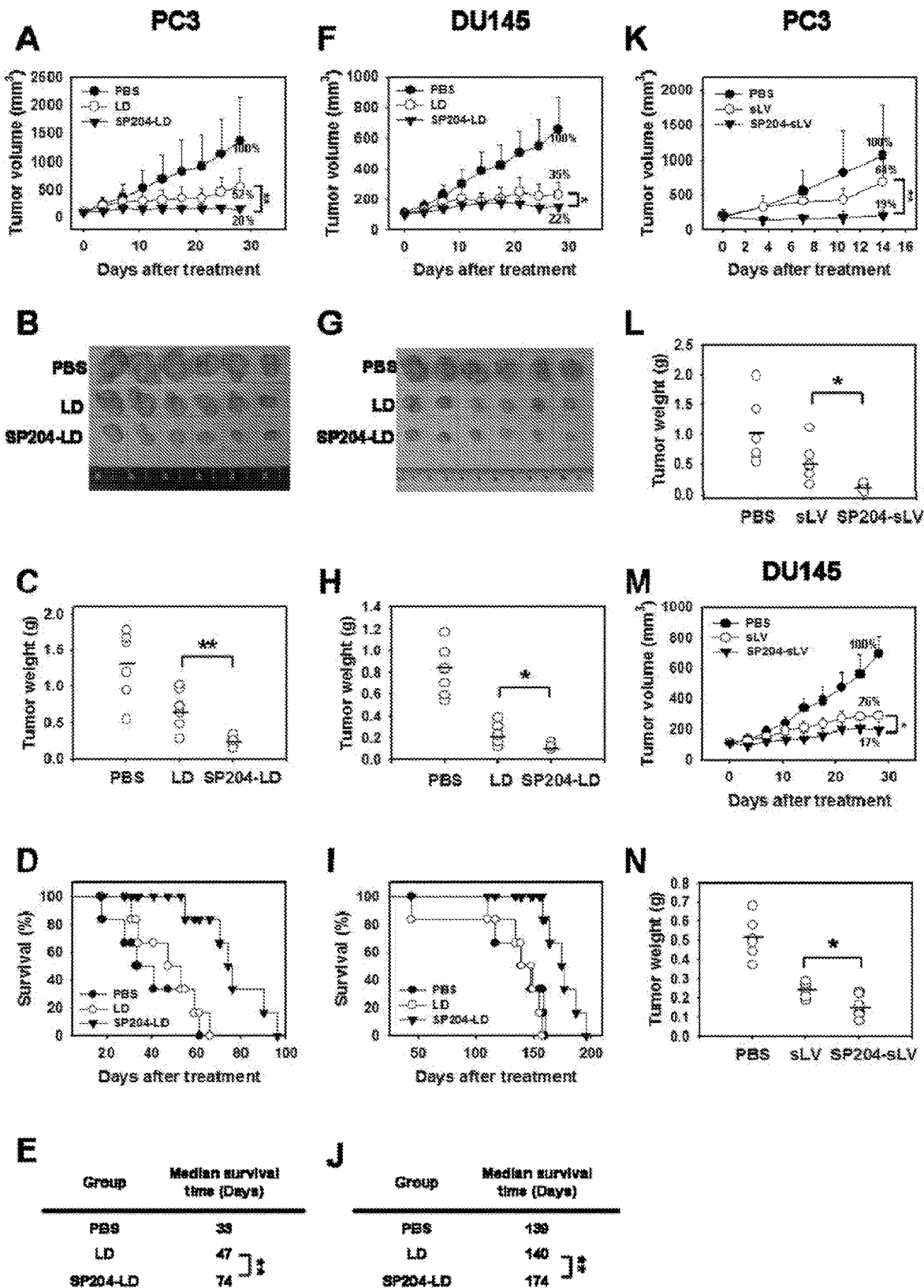

FIG. 5 shows conjugation of targeting peptide SP204 enhanced the therapeutic efficiency of drugs and prolonged the survival rate of a prostate cancer xenograft model. Mice bearing xenografts of PC3 (A-E) or DU145 (F-J) prostate cancer were treated with 1 mg/kg SP204-LD, 1 mg/kg LD, or PBS. In addition, 1 mg/kg SP204-sLV, 1 mg/kg sLV, or PBS also were injected into mice bearing PC3 (K and L) or DU145 (M and N) xenografts. All compounds were injected twice weekly for 2 to 4 weeks via tail vein. At the end of the treatment period, tumor tissues were dissected and weighed (B, C, G, H, L, and N). Mouse survival rates under doxorubicin treatment were observed. In the PC3 xenograft model, the median survival rates of the PBS, ID, and SP204-LD groups were 33, 47, and 74 days (D and E). In the DU145 xenograf model, the median survival rates of the PBS, LD, and SP204-ID groups were 139, 140, and 174 days (I and J). Survival analysis was calculated by log-rank, showing the probability of survival for all mice. n=6. Bar, mean±SEM. *, p<0.05; **, p<0.01.

Figure 6:
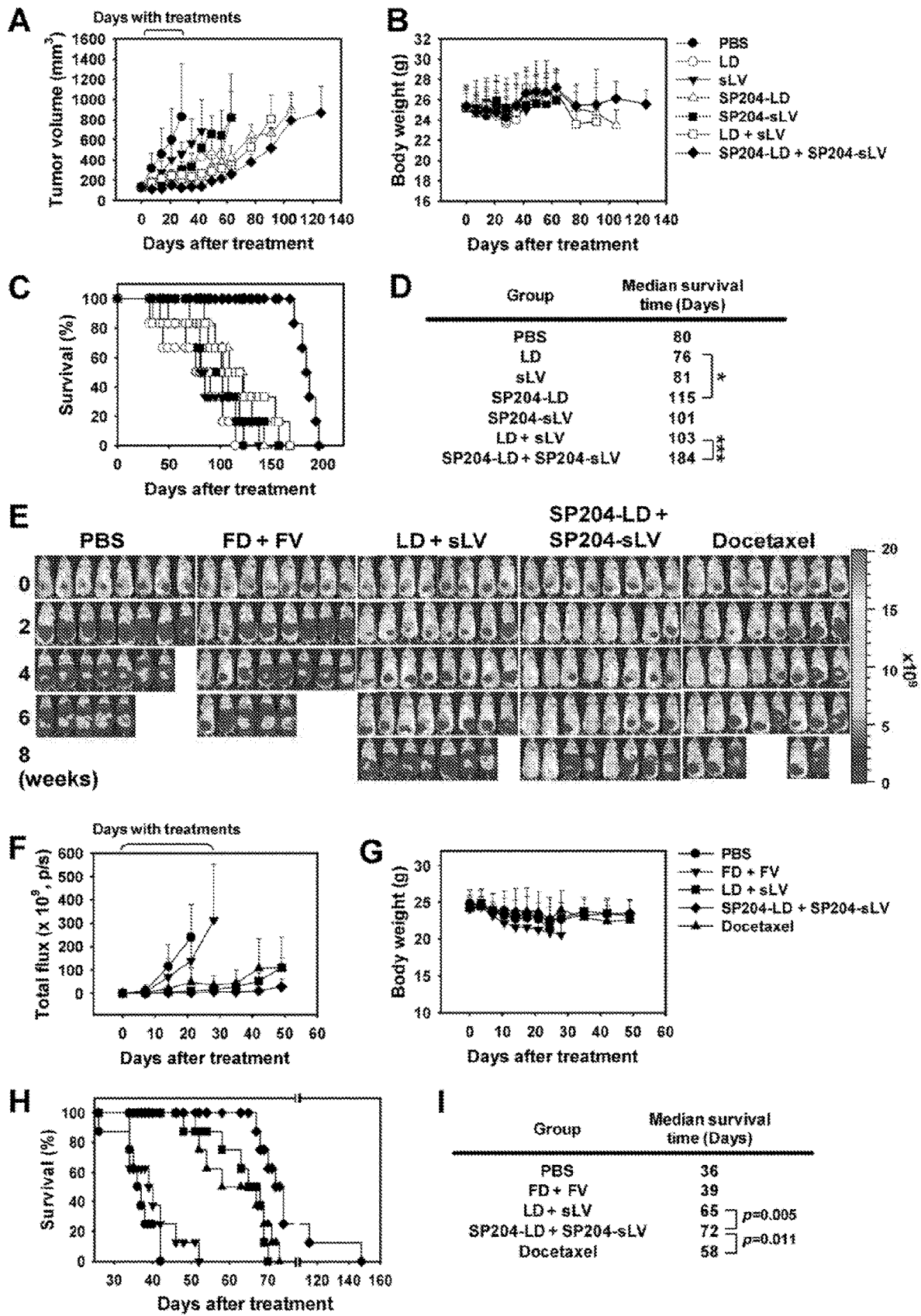

FIG. 6 shows conjugation of targeting peptide SP204 enhanced combinational therapeutic efficiency and prolonged survival rate in prostate cancer xenograft and orthotopic models. (A) Mice bearing DU145 prostate cancer xenografts were injected i.v. with LID, sLV, SP204-LD, SP204-sLV, LD+sLV, SP204-LD+SP204-sLV (1 mg/kg of doxorubicin and vinorelbine, twice a week for four weeks) or PBS (n=6). The SP204-LD+SP204-sLV treatment retarded tumor growth more effectively than other drugs. (B) Body weight of each group. (C and D) The median survival times of PBS, LD, sLV, SP204-LD, SP204-sLV, LD+sLV, and SP204-LD+SP204-sLV groups were 80, 76, 81, 115, 101, 103, and 184 days, respectively. In the orthotopic model, mice were implanted with PC3-Luc cells, and then treated with FD+FV, LD+sLV, SP204-LD+SP204-sLV, docetaxel, or PBS (n=8). Doses of 1 mg/kg doxorubicin and 2 mg/kg vinorelbine were injected i.v. twice a week. A dose of 5 mg/kg docetaxel was injected i.p. once a week. Mice were treated for 4 weeks. (E) Tumor progression was monitored by examining bioluminescence with an IVIS® 200 Image System from seven-days post-implantation. (F) Tumor progression was monitored by bioluminescence quantification. The inset shows a magnified view of the Y-axis. (G) Body weight of each group. (H and 1) The median survival rates of PBS, F)+FV, LD+sLV, SP204-LD+SP204-sLV, and docetaxel groups were 36, 39, 65, 72, and 58 days, respectively. Survival analysis was calculated by log-rank test, showing the probability of survival for all mice. *, p<0.05; ***, p<0.001.

Figure 7:
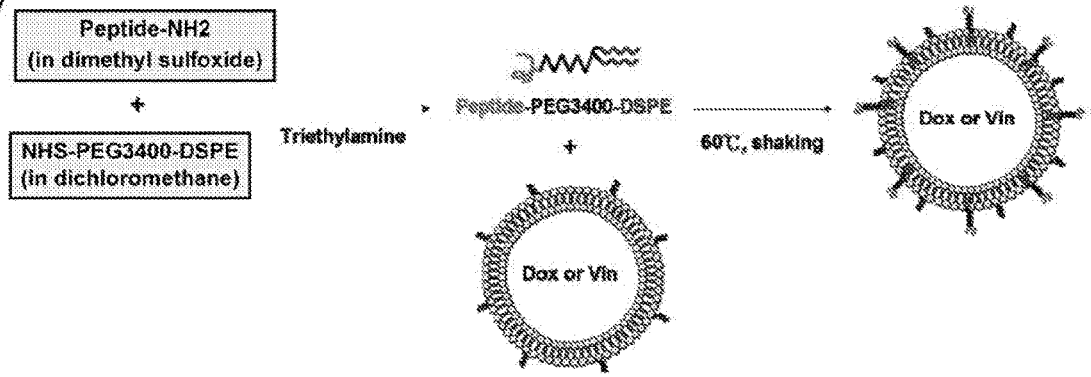

FIG. 7 is a schematic diagram showing the synthesis of peptide-targeting nanoparticles.

Figure 8:
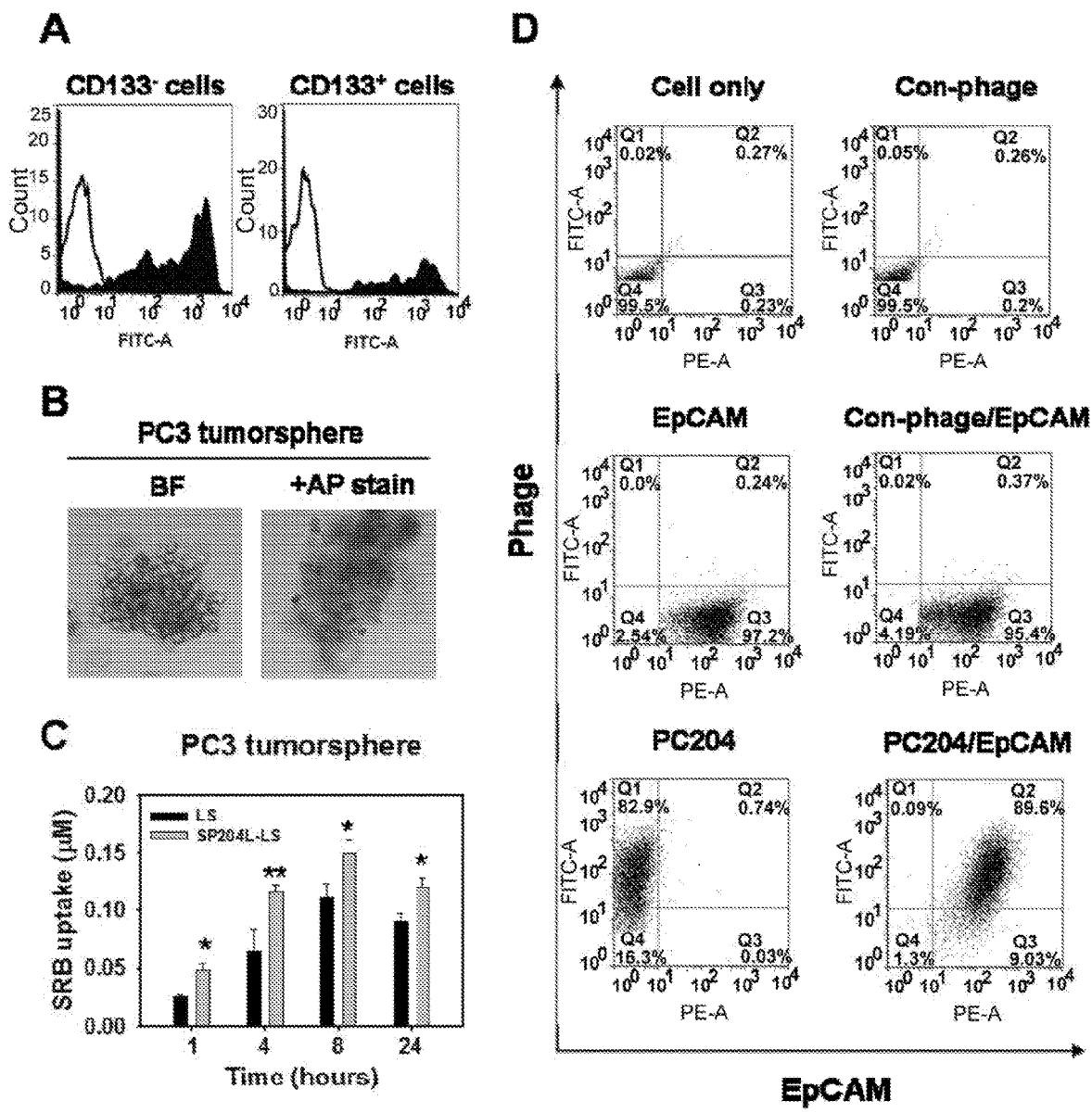

FIG. 8 shows targeting peptide enhances binding to cancer stem cell-like cells. (A) Surface-binding activity of PC204 to CD133$^-$ and CD133$^+$ PC3 cells. (B) PC3 tumorsphere formation under bright field (left) and following AP staining. (C) Internalization of SP204-LS and LS into PC3 tumorspheres. The components were cultured in 24-well plates overnight. Internalized SRB was quantified by $OD_{EX50/EM570}$ at 1, 4, 8, and 24 hours after SP204-LS or LS treatment. (D) The binding activity of the PC204 phage to EpCAM⁺ PC3 was analyzed by flow cytometry. The EpCAM/PC204-affinity subpopulation was present at greater proportions than the control phage in the PC3 cell line*, $p<0.05$; **, $p<0.01$.

DETAILED DESCRIPTION OF THE INVENTION

Definitions

Unless otherwise defined, all technical and scientific terms used herein have the same meaning as commonly understood by one of ordinary skill in the art to which this invention pertains. In the case of conflict, the present document, including definitions will control.

The term "treating" or "treatment" refers to administration of an effective amount of the compound to a subject in need thereof, who has cancer, or a symptom or predisposition toward such a disease, with the purpose of cure, alleviate, relieve, remedy, or ameliorate the disease, or the symptoms of it. Such a subject can be identified by a health care professional based on results from any suitable diagnostic method.

"An effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

The terms "anti-cancer drug" and "chemotherapeutic agent" are interchangeable.

Fluorescein isothiocyanate (FITC) is yellow-orange in color with an absorption maximum at 495 nm.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses a "therapeutically effective amount" may be obtained by calculations from the following formula:

$HED$=animal dose in mg/kg×(animal weight in kg/human weight in kg)$^{0.33}$.

Abbreviation: castration-resistant prostate cancer (CRPC); phage clone 204 (PC204); sulforhodamine B (SRB); liposome-encapsulated SRB (LS); superparamagnetic iron oxide nanoparticles (SPIONs); circulating tumor cell (CTC); cancer stem cells (CSCs); alkaline phosphatase staining (AP staining); phycoerythrin (PE).

Here, we used a phage display random peptide library to identify a new peptide, SP204, which can bind to prostate cancer cells. The diagnostic potential and biodistribution profiles of peptide-conjugated superparamagnetic iron oxide nanoparticles (SPIONs) and liposomal drugs in tumors and normal organs were compared with those of non-targeting drugs. Targeted nanomedicine was observed to have antitumor activity and increase the survival of mice bearing human prostate cancer in both xenograft and orthotopic models. Our results suggest that SP204 has considerable potential for the development of diagnostic tools and targeted drug delivery systems against prostate cancer.

EXAMPLES

Materials and Methods
Cell Lines

PC3, DU145, and LNCaP human prostate cancer cell lines and 293T human kidney cells were incubated in RPMI (PC3 and LNCaP), MEM (DU145), and DMEM (293T) medium supplemented with 10% FBS, under 5% $CO_2$ at 37° C.

Phage Display Biopanning Procedures

Biopanning procedures were carried out as described previously. Briefly, PC3 cells were grown to nearly 80% confluence and treated with $2\times10^{11}$ phages from Ph.D.-12 (New England Biolabs) in serum-free medium at 4° C. for 1 hour. After washing with PBS, phages were harvested with RIPA buffer, followed by amplification and titer-detection using the ER2738 E. coli, strain. The above biopanning steps were repeated 5 times, and phage clones were then randomly selected to culture for cellular ELISA screening.

Cellular ELISA Analysis

The cells were seeded onto a 96-well ELISA plate overnight, and then fixed with 2% paraformaldehyde for 30 min at room temperature. After washing, the cells were incubated with 5% skimmed milk overnight at 4° C. Following the removal of surplus milk, the selected phage clones were added and incubated for 1 hour. After three washes with PBS, the cells were incubated with horseradish peroxidase (HRP)-conjugated mouse anti-M13 antibodies (1:2000 dilution) for 1 hour. After repeating the washing step, the plates were incubated with peroxidase substrate o-phenylenediamine dihydrochloride plus $H_2O_2$. The reaction was terminated by the addition of 3N HCl, and the absorbance at 490 nm was measured with an E LISA reader (Model 680, BioRad).

Flow Cytometry Analysis

The prostate cancer and control cell lines were collected using 10 mM EDTA in PBS. A total of $4\times10^8$ to $5\times10^9$ pfu phages were added to $2\times10^5$ cells and incubated at 4° C. for 1 hour. The samples were incubated with anti-M13 mAbs at 4° C. for 1 hour before being incubated with PE- or FITC-conjugated anti-mouse Fab Abs at 4° C. for 30 min. The signals were analyzed by flow cytometry.

In Vivo Homing Experiments and Examination of Tissue Distribution of Phages

SCID mice were injected s.c. with $5\times10^6$ prostate cancer cells. Once the prostate cancer xenografts reached a suitable size (about 200~300 mm³), the mice were injected i.v. with $2\times10^9$ pfu phages in the presence or absence of 100 μg synthetic peptides. After ten minutes, the mice were sacrificed and perfused with 50 ml PBS to remove unbound phages. Selected organs and xenograft tumors were removed, and the phage titer recovered by E. coli strain ER2738 was measured using IPTG/X-Gal spray. Partial organs and tumors were embedded using optimal cutting temperature compound (O.C.T.) to prepare sections for immunohistochemical staining.

Immunohistochemical Localization of Phages in Xenograft Tumor Sections

The tissue samples from in vivo phage homing experiments were embedded in frozen blocks. Phage distribution in each tissue was assessed by first removing O.C.T. with cold PBS, and then fixing the frozen sections with 4% paraformaldehyde for 10 min. The sections were incubated with 1% BSA for 30 min to block non-specific binding. After washing, the sections were incubated with mouse anti-M13 antibodies at a dilution of 1:250 for 1 hour, followed by treatment with polymer-based SUPER SENSITIVE™ IC detection system. In brief, the sections were incubated with SUPER ENHANCER™ reagent for 20 min and poly-HRP reagent for 30 min. DAB was used as a chromogen to visualize peroxidase activity, and the reaction was stopped by the addition of PBS. The preparations were lightly counterstained with hematoxylin, mounted with PER-MOUNT™, and examined by light microscopy.

Binding Analysis of Phage Clones to Clinical Tumor Surgical Specimens by Immunohistochemistry A human prostate cancer tissue microarray was purchased from SuperBioChips and US Biomax Laboratories. The slides were deparaffinized and antigen retrieval was performed concomitantly in the TRILOGY™ buffer system in accordance with the manufacturer's instructions. The sections were blocked with 3% $H_2O_2$ and 1% BSA for 30 min, and then 2×10 pfu/μl phages were added, and the sections incubated for 1 hour. After washing, the sections were incubated with mouse anti-M13 antibodies at a dilution of 1:250 for 1 hour, followed by treatment with polymer-based SUPER SENSITIVE™ IHC detection system.

Phage Labeling and Imaging

Phages were labeled with a fluorescent dye. HILYTE™ Fluor acid NHS ester (HILYTE™ 750, AnaSpec). Phages ($4 \times 10^{11}$ pfu) were subsequently incubated with PBS solution containing 20 nmole HILYTE™ 750. The phage/fluorochrome reaction was allowed to continue for 1 hour at room temperature in the dark. Subsequently, the volume of the labeled phage solution was made up to 1 ml with PBS, and the phages were purified by polyethylene glycol precipitation. Finally, fluorochrome-labeled phages were resuspended in PBS.

Synthesis of SP204-Conjugated Quantum Dots

Quantum dots (QDs, Invitrogen) were used for in vivo imaging studies. The procedures for synthesis of peptide-conjugated QDs were described by Lu et al. (2013) (PloS One 8, e66128). Briefly, QDs were conjugated with sulfo-SMCC (sulfosuccinimidyl 4-(N-malemidomethyl) cyclohexane-1-carboxylate; Thermo) to generate a maleimide-activated surface on QDs, and free sulfo-SMCC was removed using a NAP-5 desalting column. SP204-GGGC synthesis involved thiolation. The maleimide-functionalized QDs were incubated with SP204-GGGC at 4° C. overnight. SP204-conjugated QDs were purified using a NAP-5 desalting column to remove free QDs.

Synthesis of SP204-PEG-DSPE Conjugates

A total of 8.5 mg of NHS-PEG-DSPE [N-hydroxysuccinimido-carboxyl-polyethylene glycol (MW, 3400)-derived distearoylphosphatidyl ethanolamine] dissolved in 0.25 ml of dichloromethane was added to 0.25 ml of DMSO containing 3.1 mg of SP204 peptides. A volume of 11 μl of triethylamine was added to the mixture to catalyze the reaction. The stoichiometric molar ratio of SP204 and NHS-PEG-DSPE was 1.1:1. The reaction was gently rotated for 72 hours at room temperature. The SP204-PEG-DSPE conjugates were purified by dialysis with a 3.5 kDa cut-off membrane, and dried through lyophilization. The product was detected by MALDI-TOF by comparison with the raw materials.

Preparation of Peptide-Conjugated Liposomal Drugs

Liposomes were prepared according to the following procedure. Briefly, mixtures of DSPC, cholesterol, and $MPEG_{2000}$-DSPE (3:2:0.3 molar ratio for sulforhodamine B (SRB) and doxorubicin; 3:2:0.15 molar ratio for vinorelbine) were dissolved in chloroform and dried using a rotary vacuum evaporator to form a thin lipid film. The dried lipid film was hydrated with 250 mM ammonium sulfate (for SRB and doxorubicin) or 300 mM ammonium salts of 5-sulfosalicyclic acid (for vinorelbine) at 60° C., followed by shaking until the solution dissolved. The solution was frozen and thawed 5 times using liquid nitrogen and a 60° C. water bath. The dispersion was extruded eight times through polycarbonate filters of 100 nm using a LIPOSOFAST®-100 jacketed extruder. The phospholipid concentration was measured by Bartlett's method. Doxorubicin and vinorelbine were encapsulated using a remote loading method at a concentration of 1 mg of doxorubicin or 3.5 mg vinorelbine per 10 μmol phospholipid. SP204-PEG-DSPE was subsequently incorporated into pre-formed liposomes by shaking the mixture in a 60° C. water bath for 30 min, and then quickly placing it on ice for 10 min. The extraliposomal buffer was exchanged with HEPES buffer, and a SEPHADEX® G-50 column was used to remove released free drug, unconjugated peptides, and unincorporated conjugates. Doxorubicin concentrations were determined by measuring fluorescence at $\lambda_{EX/EM}$=485/590 nm using an ELISA reader. Vinorelbine concentrations were determined by HPLC. The zeta average size of vesicles was analyzed using a Malvern Zetasizer Nano ZS.

MTT Cell Proliferation Assay

The cells were seeded onto 96-well plates (4000 cells/well). After overnight incubation, liposomal drugs were added to the cells in the absence or presence of SP204 for 24 hours, and then the cells were incubated in medium without drugs for 48 hours. Finally, MIT reagent and DMSO were added after an additional 3 to 4 hours of incubation to determine the absorbance at 540 nm using an ELISA reader (SPECTRAMAX® M5).

Uptake of SP204-LS and SP204-SPIONs by Prostate Cancer Cells

Cells were seeded in 24-well plates ($2 \times 10^5$ cells/well) overnight liposomal SRB was then added 0.17, 0.5, 1, 4, 8, and 24 hours later. Intracellular SRB was examined by lysing cells with 1% TRITON™ X-100 after washing with PBS. The cell lysates were centrifuged at 12,000 rpm for 5 min and the fluorescence intensity was determined using an ELISA reader at $\lambda_{EX/EM}$=520/570 nm.

Iron uptake was measured by transferring PC3 cells to culture medium containing 10 μg/ml superparamagnetic iron oxide nanoparticles (SPIONs) or SP204-SPIONs, and incubating the cells for 4 hours at 37° C. Free nanoparticles were removed by washing with PBS and the cells were incubated with Prussian blue reagent, stained with nuclear fast red solution, and observed by light microscopy.

Localization of SP204 in Prostate Cancer Tissues

SP204-SPIONs were prepared by conjugating SP204 to the $Dex-Fe_3O_4$ nanoparticles. Each $Dex-Fe_3O_4$ nanoparticle can be linked to more than ten SP204 molecules. After the paraffin-embedded xenograft sections were deparaffinized and retrieved using the TRILOGY™ buffer system, the sections were incubated for 12 hours with SPIONs or SP204-SPIONs (40 μg/ml) at 4° C., washed, and then incubated for 30 min with routine Prussian blue reagents, containing 5% potassium ferricyanide +5% HCL (1:1). This was followed by counter staining for 5 min with nuclear fast red solution. The preparations were mounted with PER-MOUNT™, and observed by light microscopy. SPION and SP204-SPION homing assays were performed largely as described in the "In vivo homing experiments" section above, except that the incubation for 12 hours at 4° C. was omitted.

In Vivo Imaging of Human Prostate Cancer Xenogrfts Using SP204-QDs and SP204-SPIONs Six- to eight-week-old SCID mice were injected s.c. with PC3 or DU145 prostate cancer cells. Once the tumor size reached about 200 $mm^3$, HILYTE™ 750-conjugated phages or QD-conjugated peptides were injected through the tail vein. Fluorescence images of HILYTE™-750 and QDs were captured using an IVIS9@ 200 imaging system. Tumor accumulation of HILYTE™ 750 and QDs were quantitatively compared by subtracting background from fluorescence intensity using LIVING IMAGE® Software (Xenogen).

For animal MRI experiments, a 7 Tesla MRI system (Bruker. USA) was used for better resolution. We chose TurboRARE-T2 pulse sequences (TR/TE 3000/32.862 ms, flip angle 180, and matrix size 256×256) for better T2-weighted imaging. The slice thickness was 1 mm with a 1 mm gap, the field of view (FOV) was 8.5×4 cm for the coronal scanning of the test tubes, and a scan time of 6 min and 24 s was used for sagittal scanning at the NEX of 4. The images were then analyzed at the workstation provided by Bruker healthcare.

Animal Model for the Study of Peptide-Targeted Therapy

A total of 5×10$^6$ prostate cancer cells were injected s.c. into the dorsolateral flank of six-week-old SCID mice. Liposomal drugs with or without SP204 were injected through the tail vein when the tumor size approached 150 mm$^3$. Mouse body weights and tumor sizes were measured twice a week. At the end of the experiment, some organs and tumors were embedded in O.C.T. compound.

Terminal Deoxynucleotidyl Transferase-Mediated dUTP Nick End Labeling (TUNEL) Staining The fixed sections were incubated with TUNEL reaction mixture (Roach Diagnostics) at 37° C. for 1 hour and counterstained with DAPI reagent. The slides were visualized under a fluorescence microscope and quantified using METAMORPH® software.

CD31 Staining

The fixed sections were incubated with rat anti-mouse CD31. After secondary antibody incubation, the slide was counterstained with DAPI reagent. The slides were then visualized under a fluorescence microscope and quantified with METAMORPH® software.

Orthotopic Implantation and Therapeutic Studies

PC3 cells were transfected with *Lenti*-Luc virus (lentivirus containing the luciferase gene), and a stable PC3-Luc cell line was selected by puromycin screening. PC3-Luc cells (5×10$^5$ cells in 20 μl PBS per mouse) were orthotopically transplanted into the dorsal lobe of the prostate of SCID mice after anaesthesia with Avertin at a dose of 250 mg/kg. Seven days later, all mice bearing tumors were randomly divided into five groups (n=8 per group) based on photon flux indices detected using Xenogen IVIS® 200 Luminal Image. Tumor-bearing mice were treated with different formulations of anti-cancer drugs or PBS. Tumor development was recorded every 7 days. The body weights and survival rates were measured.

Statistical Analysis

Student's t-test was used to calculate the P values for mouse body weight changes. Survival rates were determined with Kaplan-Meier survival curves. Significant differences were determined with log rank test.

Results

Identification of Novel Peptides that Bind to Prostate Cancer Cells

Figure 1:
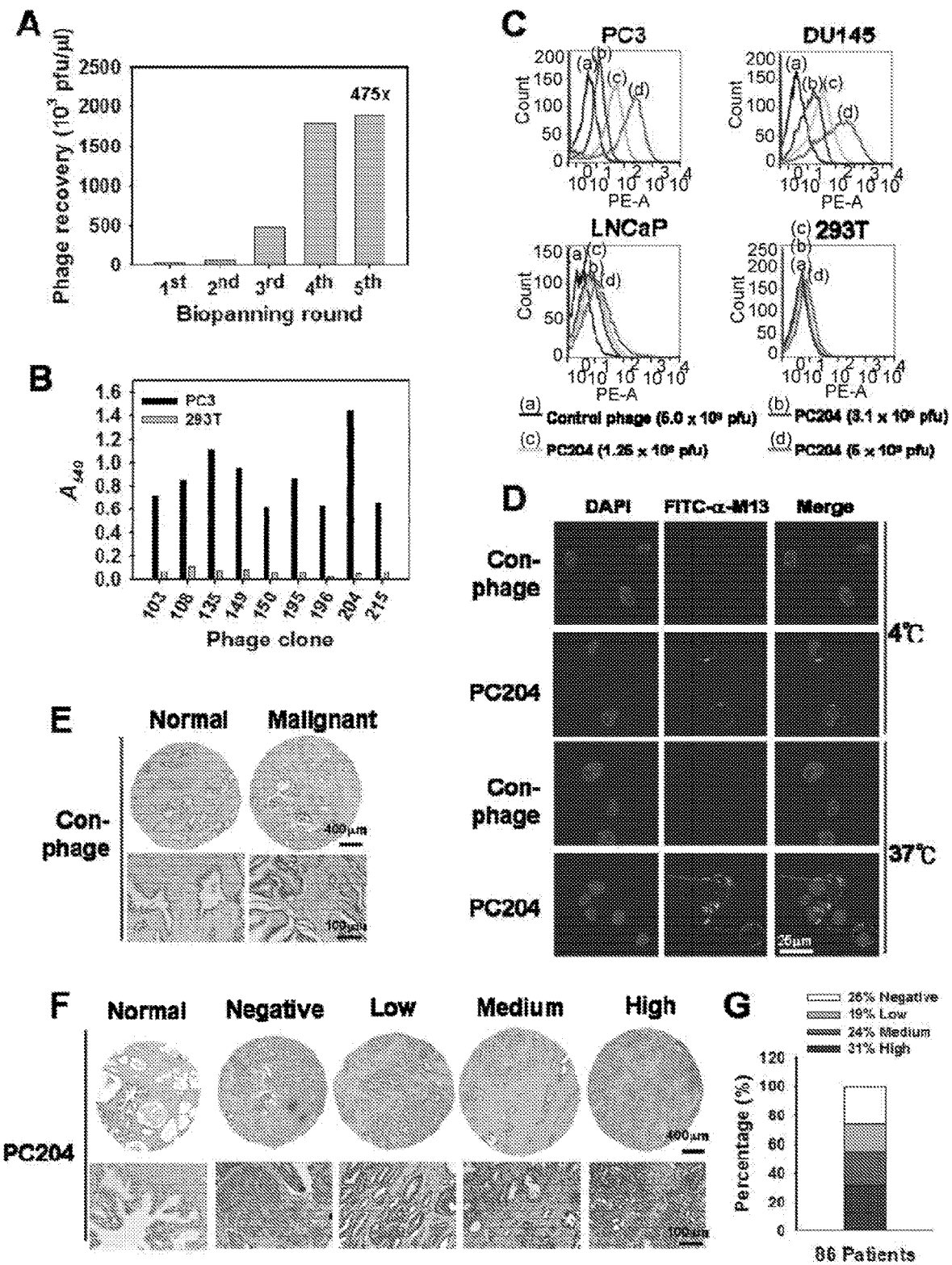
FIG. 1 shows identification of peptides with affinity for prostate cancer cells through phage display assay in vitro. (A) Phage-display was used to select peptides that bound to the PC3 prostate cancer cell line. After five rounds of biopanning, the titer of phage eluted from PC3 had increased by 475-fold compared to the first round of selection. Pfu, plaque-forming units. (B) Binding activity and specificity between individual phage clones and PC3 cells were tested by cellular ELISA. $A_{549}$, optical density at 549 nm. (C) The binding activities of the PC204 phages to PC3, DU145, and LNCaP prostate cancer cell lines were analyzed by flow cytometry. PC204 increased relative fluorescence intensity in a dose-dependent manner for cancer cell lines, but not for 293T cells. (D) Confocal image showing the binding and internalization ability of PC204 at 4° C. and 37° C. The phages were recognized with mouse anti-M13 antibodies, and then probed by FITC-conjugated goat anti-mouse IgG. No FITC signal was detected with control phage (con-phage). DAPI was used to stain nuclei. Immunohistochemical staining of human prostate cancer tissue microarray using control phage (E) or PC204 phage (F). Binding activities of PC204 were determined on the basis of the staining intensity. (G) Extent of binding of PC204 to a tumor microarray derived from prostate cancer patients. Phycoerythrin (PE), a red protein-pigment complex, is conjugated to antibody for flow cytometry analysis. The machine calculates the total area signal of PE, called PE-A.

We used a phage-displayed random peptide library to isolate phages that were able to bind PC3 prostate cancer cells. After five rounds of affinity selection, the recovery rate of the fifth round was 475-fold greater than that of the first round (FIG. 1A). Phage clones were randomly isolated, and their ability to react with prostate cancer cells and normal cells was examined by cellular ELISA assay. Nine phage clones that demonstrated relatively high reactivity toward prostate cancer cells but no reactivity toward 293T (FIG. 1B) were selected and sequenced (Table 1). Flow cytometry analysis was performed to identify phage clones that specifically bound to PC3 prostate cancer cells, but not to intracellular molecules: phage clone 204 (PC204) was found to be highly reactive toward prostate cancer cells, whereas the other eight phage clones exhibited weak binding activity. Table 1 shows alignment of phage-display peptide sequences selected by PC3 cells.

TABLE 1

| Peptide Name | Amino acid sequence | SEQ ID NO: |
|---|---|---|
| SP103 | FPWTEPSYKQGD | 1 |
| SP108 | FPWTEPLYKYGE | 2 |
| SP135 | FPWTEPSYKYGD | 3 |
| SP149 | MPWKESAWLEKI | 4 |
| SP150 | MPWTEPNYLLTQ | 5 |
| SP195 | IPWKESACLAKI | 6 |
| SP196 | APWLEGSYKTVY | 7 |
| SP204 | KQFSALPFNFYT | 8 |
| SP215 | SEFPRSWDMETN | 9 |

We incubated three prostate cancer cell lines (PC3, DU145, and LNCaP) with different concentrations of phages. Analysis by fluorescence-activated cell sorting revealed that PC204 reacted strongly with PC3 and DU145, but exhibited only moderate reactivity toward LNCaP (FIG. 1C). The 293T cell line was poorly recognized by all phage clones tested. PC3 or DU145 were incubated with PC204 or control phage at either 4° C. or 37° C. for 30 min. PC204 was observed to be distributed on the plasma membrane by incubation at 4° C. When the cells were incubated at 37° C., fluorescent signals were found to be internalized and diffused throughout the cytoplasm (FIG. 1D)).

We subjected human prostate cancer tissue arrays to immunohistochemical staining of PC204. Prostate adenocarcinoma was not recognized by control phage (FIG. 1E), but was bound by PC204 (FIG. 1F). Of the 86 prostate cancer specimens from different patients, 74% (64/86) exhibited positive PC204 staining (FIG. 1G). The data indicate that PC204 can recognize unidentified molecules expressed on prostate cancer cell lines, and cells from surgical specimens of prostate cancer.

Animal Model for Studies of PC204 Tumor Targeting

Figure 2:
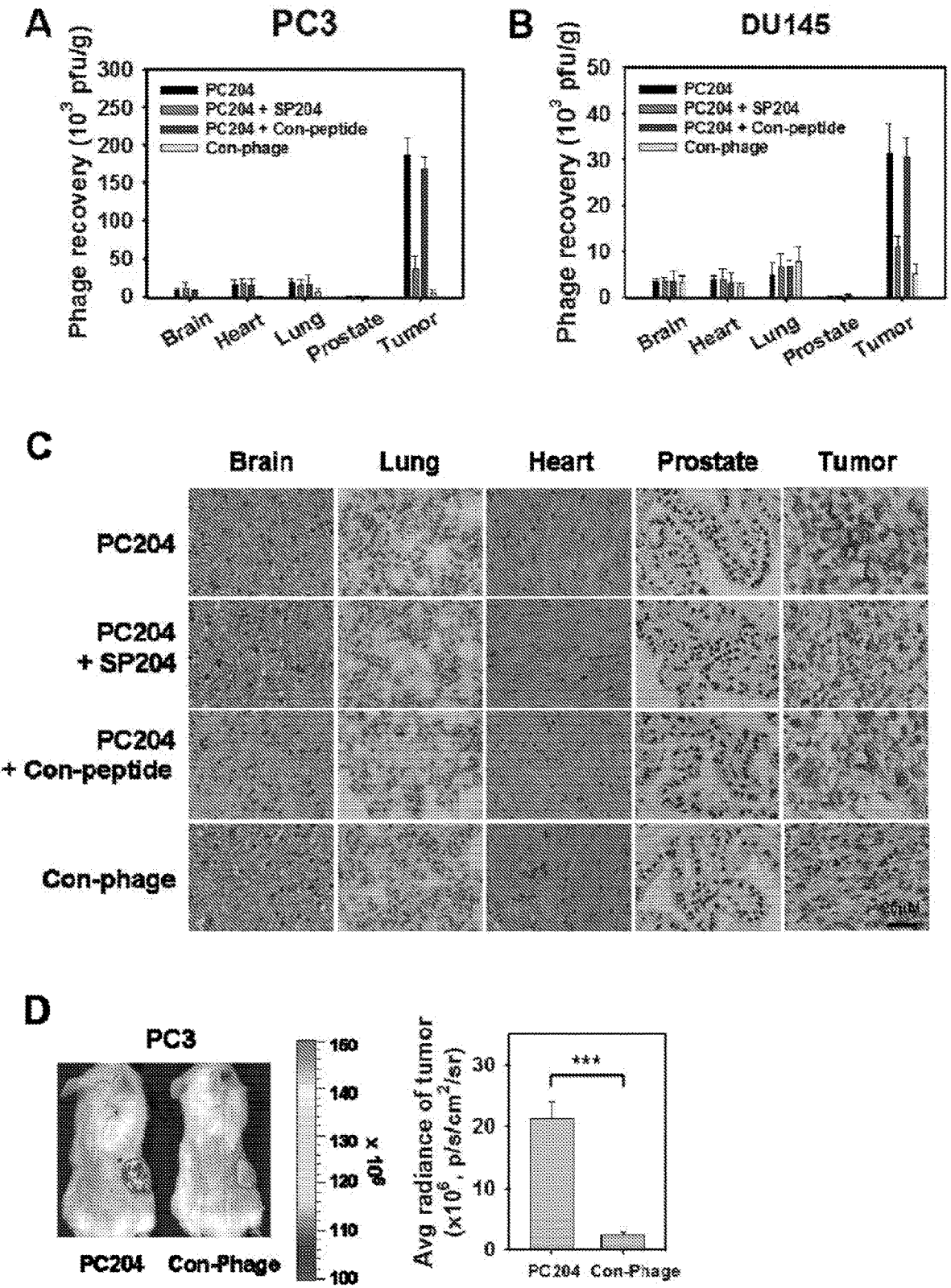
FIG. 2 shows verification of the tumor-homing ability of PC204 in vivo. Mice bearing PC3 (A) or DU145 (B) prostate cancer xenografts were injected with PC204 or control phage (con-phage) through the tail vein. The targeting activity of PC204 to tumor tissue was competitively inhibited by its synthetic peptide (SP204), but not by the control peptide (con-peptide). (C) Immunohistochemical detection of PC204 localization after i.v. injection into SCID mice bearing PC3 prostate cancer xenografts. Phage immunoreactivity was observed to be localized in tumor tissue, but not in normal organs such as brain, lung, heart, and prostate. Neither tumor cells nor normal organs exhibited control phage immunoreactivity. (D) SCID mice bearing PC3 prostate tumors were injected with HILYTE FLUOR™ 750-labeled PC204 or control phage for 24 hours. In vivo fluorescence imaging of tumor is indicated by the red circle. The fluorescence signals of tumor were quantified using IVIS® 200 software, n=3, ***p<0.001.

To investigate the tumor targeting ability of PC204 in vivo, we intravenously injected phages into the tail vein of mice bearing PC3- (FIG. 2A) or DU145-derived (FIG. 2B) tumor xenografts. Tumor homing ability was determined from the phage titer ratio of tumor to normal organs, as compared to that of control phage (FIGS. 2A and 2B). PC204 exhibited strong tumor homing ability, with phage concentrations 6 to 20-fold higher in the tumor mass than in normal organs (including the brain, lung, heart, and prostate). Control phage (Con-phage), however, revealed no such homing ability (FIGS. 2A and 2B). The tumor homing abilities of the PC204 phage were further confirmed by peptide competitive inhibition experiments. Mice bearing PC3 or DU45 xenografts were co-injected with PC204 and its cognate synthetic peptide, SP204. Co-injection of synthetic peptide SP204 with PC204 inhibited the recovery of PC204 from tumor tissue. SP204 inhibited the ability of PC204 to bind to PC3 and DU145 tumor tissue by 5.2- and 2.87-fold, while the same concentration of a control peptide showed no such inhibitory effect (FIGS. 2A and 2B).

To verify the distribution of PC204, we immunostained tissue sections of tumors and normal organs derived from the homing and competition experiments using anti-phage antibody (FIG. 2C). PC204 phages targeted tumor tissues, but not normal organs. However, no immunoreactivity was observed in tumor tissue co-injected with PC204 and the cognate synthetic peptide SP204. Neither tumor cells nor normal organs were found to be immunoreactive towards control phage (FIG. 2C). We injected HILYTE™ 750-labeled phage into a mouse tumor model to determine phage homing ability by tumor imaging. SCID mice bearing PC3- or DU145-derived xenografts were injected i.v. with PC204-HILYTE™ 750 or control phage-HILYTE™ 750, and fluorescent images were monitored by IVIS® 200 from 24 h after injection. The fluorescent intensity of the tumor area of PC204-HILYTE™ 750-injected mice was increased by 7.6- and 6.5-fold, compared to con-phage-HILYTE™ 750-injected mice from PC3- or DU145-derived xenografts, respectively (FIG. 2D). Together, these results indicate that PC204 phage has tumor targeting ability towards prostate cancer xenografts in vivo.

SP204-Conjugated Liposomes Exhibit Enhanced Drug Intracellular Delivery and Cytotoxicity We synthesized the peptide ligand (SP204) displayed on PC204, and coupled this ligand to NHS-PEG$_{3400}$-DSPE to form SP204-PEG$_{3400}$-DSPE. Following insertion of the phospholipid DSPE, the SP204-PEG$_{3400}$-DSPE conjugates were coupled to the external surface of liposomal nanoparticles containing sulforhodamine B (SRB), doxorubicin, or vinorelbine (FIG. 7).

Figure 3:
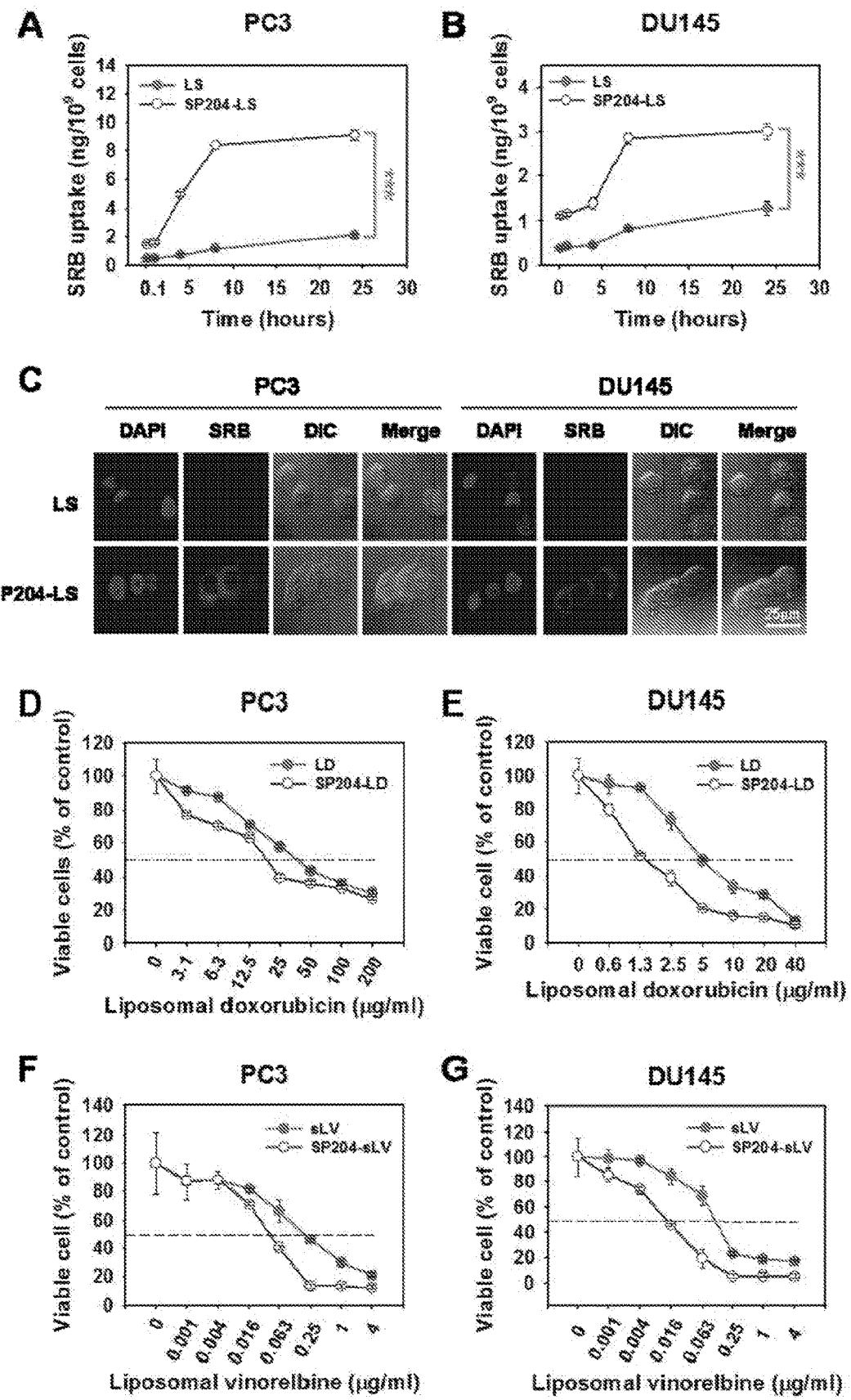
FIG. 3 shows SP204 enhanced liposomal SRB, liposomal doxorubicin (LD), and stable liposomal vinorelbine (sLV) binding and internalization to human prostate cancer cell lines. Internalization studies of SP204-LS and LS in PC3 (A) and DU145 (B) prostate cancer cell lines. The cells were cultured in 24 well plates (2×10$^4$ cells/well) overnight. Internalized SRB was quantified based on $OD_{EX520/EM570}$ at 0.167, 1, 4, 8, and 24 hours after treatment with SP204-LS or LS (10 µM). (C) PC3 and DU145 cells were incubated with 10 µM SP204-LS or non-targeting LS at 37° C. for 30 min. DAPI was used for nuclear staining. Cell shape was observed with the differential interference contrast (DIC) model. For the in vitro cytotoxicity assay, PC3 (D and F) and DU145 (E and G) were treated with LD, SP204-LD, sLV, or SP204-sLV at varying concentrations. Cell viability was analyzed by MTT assay and calculated as a percentage of living cells. The black dashed line shows mean 50% viability. ***, p<0.001.

A larger amount of SRB was observed in prostate cancer cells treated with SP204-LS than cells incubated with non-targeting LS (FIGS. 3A and 3B). While cells treated with SP204-LS contained internalized SRB around the cytoplasm, cells treated with LS alone did not (FIG. 3C). These results indicate that SP204 can bind to the surface of prostate cancer cells and induce the receptor-mediated endocytosis of LS.

To assess whether SP204 can enhance the therapeutic potential of liposomal doxorubicin (LD), we performed in vitro cytotoxicity assays for SP204-LD in PC3 and DU145 cells. The half maximal inhibitory concentration (IC$_{50}$) of SP204-LD was 2.0- and 3.4-fold lower than that of LD in PC3 and DU145 cells, respectively (FIGS. 3D and 3E). Moreover, we also developed a stable vinorelbine-loaded targeting liposome (sLV), into which SP204-PEG$_{3400}$-DSPE was inserted. The IC$_{50}$ of SP204-conjugated liposomal vinorelbine (SP204-sLV) was found to be 4.5- and 10.1-fold, lower than that of sLV in PC3 and DU145 cells, respectively (FIGS. 3F and 3G).

In Vivo Tumor Imaging of SP204-QD and SP204-SPIONs

Figure 4:
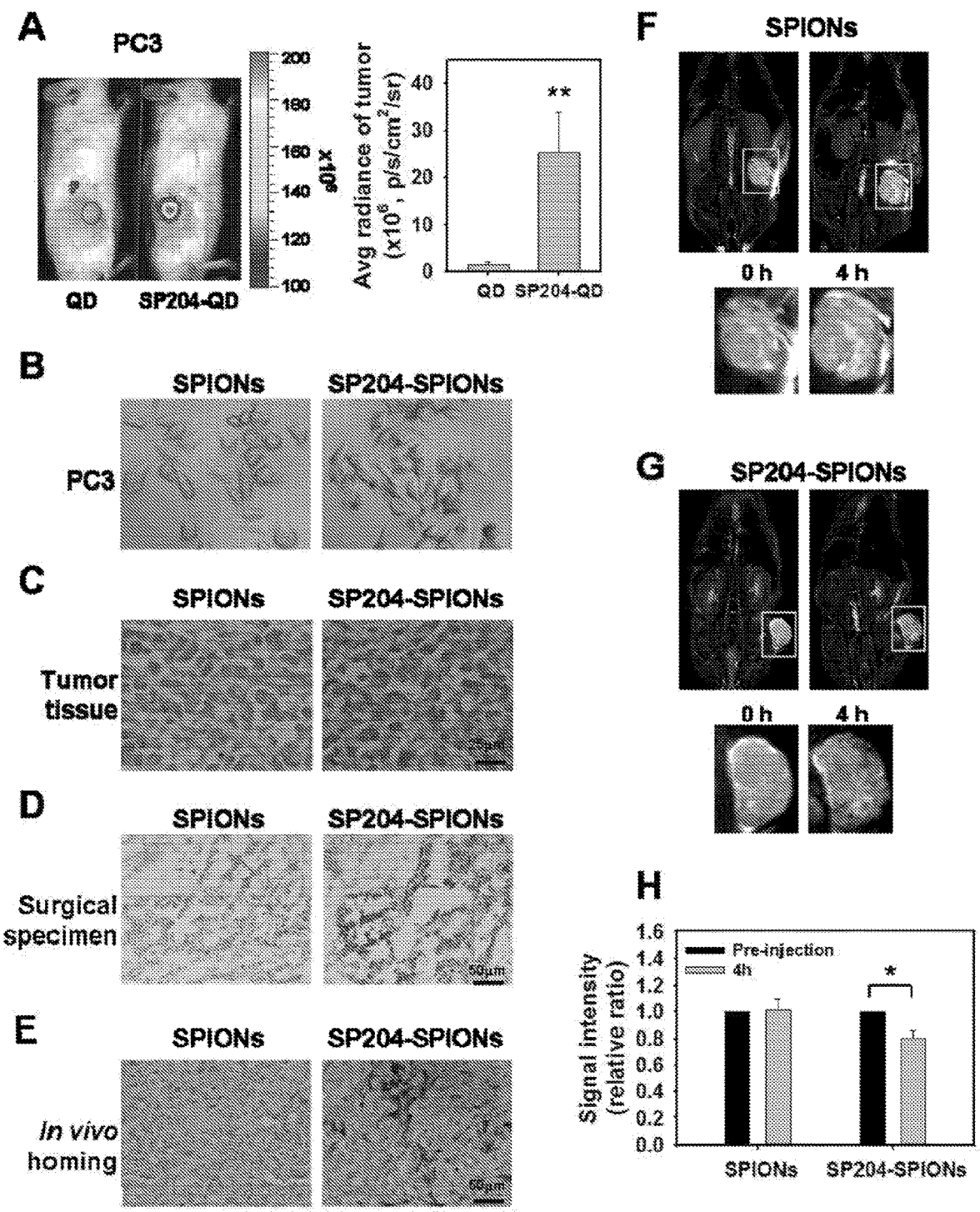
FIG. 4 shows in vivo tumor targeting and imaging with SP204-conjugated quantum dots and SPIONs. (A) In vivo fluorescence imaging of SCID mice bearing PC3-derived tumors was performed after intravenous injection of QD or SP204-QD for 6 hours. Red circles indicate tumor loci. The fluorescence intensity of the tumor area was quantified using IVIS software (n=3). (B) Microscope image of Prussian blue-stained iron in PC3 cells after 4 hours of incubation with 10 µg/ml SPIONs or SP204-SPIONs. Cells treated with SP204-SPION contained blue spots, indicative of the presence of iron oxide particles. Paraffin sections from PC3 xenografts (C) and surgical tissue sections from prostate cancer patients (D) were treated with 40 µg/ml SPIONs or SP204-SPIONs for 12 hours, and then stained with Prussian blue reagent. Blue granular reaction products were observed in the SP204-SPIONs group, but not in the SPION group.

We injected SP204-conjugated quantum dots (SP204-QD) or non-conjugated quantum dots (QD) into mice bearing PC3- or DU145-derived xenograns. At 4 hours post-injection, the near-infrared fluorescence signal intensity in the tumor area of SP204-QD-treated mice was increased by 16.6- and 5.2-fold, compared to QD-treated mice from PC3- or DU145-derived xenografts, respectively (FIG. 4A). We further examined the cellular uptake of Superparamagnetic iron oxide nanoparticles (SPIONs) to determine whether SP240-conjugated SPIONs (SP204-SPIONs) are suitable for enhancing tumor imaging. PC3 cells were incubated with SP204-SPIONs or SPIONs for 4 hours, and the cells were then stained with Prussian blue. We observed higher iron oxide concentrations within PC3 cells treated with SP204-SPIONs than cells incubated with non-targeted SPIONs (FIG. 4B), confirming that conjugation of SP204 to SPIONs facilitates cellular uptake. Substantial Prussian blue granular reaction staining was observed in PC3 xenograft paraffin sections (FIG. 4C) and surgical specimens from prostate cancer patients (FIG. 4D) incubated with SP204-SPIONs, as compared to sections treated with SPIONs.

Tumor-specific accumulation and MRI suitability of SP204-SPIONs in vivo were investigated in tumor-bearing mice under an external magnetic field. At four hours after injection of PC3 tumor-bearing mice with SP204-SPIONs or SPIONs, we stained paraffin sections from these xenografts with Prussian blue. Xenograft sections of the SP204-SPIONs group contained sporadically-located blue granular reaction products (FIG. 4E). These tumors showed a significant signal intensity drop during T2-weighted MRI (FIG. 4G). No Prussian blue staining or MRI signals were observed following treatment with SPIONs (FIGS. 4E and 4F). While the signal intensity ratio between the post- and pre-contrast images of tumors from mice injected with SP204-SPIONs decreased by 20.1%, no change was observed for tumors from mice injected with SPIONs (FIG. 4H).

Pharmacokinetics and Biodistribution of SP204-LD

The pharmacokinetic properties and biodistribution of free doxorubicin, LD, and SP204-LD were determined by administering these drugs to NOD/SCID mice at a matched dose of 2 mg doxorubicin/kg through tail vain injection. Blood samples were drawn at selected time points, and quantities of doxorubicin were analyzed. Free doxorubicin had a poor pharmacokinetic profile, possibly because its small size (Mr. 543.54) causes it to be efficiently cleared through the kidney. The LD and SP204-LD groups exhibited a similar decline in doxorubicin concentrations over time, suggesting that conjugation with SP204 may not affect interactions with plasma proteins or influence the plasma pharmacokinetics of LD in vivo.

At 24 hours after injection, the mean intra-tumor doxorubicin concentrations in the SP204-LD group were 6.1- and 2.6-folds higher than that in the FD and LD groups, respectively. The tumor doxorubicin AUC$_{0-48}$ were 4.27, 9.82, and 26.02 µg·h/g in the FD, LD and SP204-LD groups, respectively. Distribution of SP204-LD in all normal organs was highly similar to that of LD at each time point examined.

Therapeutic Efficacy of SP204-Mediated Targeting Liposomes in Mouse Models

We injected SCID mice bearing PC3-derived xenografts with LD SP204-LD, or equivalent volumes of PBS through the tail vein (1 mg/kg every 3.5 days, for six injections with a total cumulative dose of 6 mg/kg). At the end of the treatment period, the tumor size of the LD group gradually increased to 3.0-fold that of the SP204-LD group (FIG. 5A). The final average tumor weight in mice treated with SP204-LD was 0.23 g, compared to 0.69 g in mice treated with LD and 1.30 g in mice treated with PBS buffer (FIGS. 5B and 5C). The significant reduction in tumor weight demonstrated the superior inhibition efficacy of SP204-L D as compared to LD. The SP204-LD and LD groups did not exhibit significant changes in body weight during the treatment period. SP204-LD could increase median overall survival rates in the mouse xenograft model (FIGS. 5D, 5E): the median survival rate of the SP204-LD group was 74 d, significantly longer than 47 d for the LD group and 33 d for the PBS group (FIGS. 5D and 5E).

Marked disseminated necrotic/apoptotic areas showed greater dissemination in the SP204-LD group than in the LD and PBS groups. Anti-CD31 antibodies were used to detect tumor blood vessels, and terminal deoxynucleotidyl transferase-mediated dUTP nick end labeling (TUNEL) was used to identify apoptotic cells. Representative fluorescent microscopic fields of tumors revealed a lower density of blood vessels and more apoptotic tumor cells in the SP204-LD-treated group than that in LD-treated or PBS groups. There were significantly fewer areas containing $CD31^+$ endothelial cells in the SP204-LD-treated group than in the LD and PBS groups. More apoptotic cells in the SP204-LD-treated group than in the LD and PBS-treated groups. Similar results were observed in studies using DU145 xenografts: SP204-LD treatment inhibited tumor growth, as compared to LD treatment (FIGS. 5F, 5G, and 5H), while body weight was not affected by any of the drugs during the treatment period. SP204-LD could increase median overall survival rate in mice bearing DU145-derived xenografts (FIGS. 5I, 5J). The median survival rate of the SP204-LD group was 174 d, which was significantly longer than 140 d for the LD group and 139 d for the PBS group (FIGS. 5I and 5J). There were more necrotic/apoptotic areas and fewer blood vessels in the SP204-LD group than in the LD group.

We examined the efficacy of SP204-sLV at inhibiting tumors in SCID mice bearing PC3-derived xenografts. Treatments were administered through tail vein injection (1 mg/kg every 3.5 days, for four injections with a total cumulative dose of 4 mg/kg). At the end of the treatment period, the tumor size of the sLV group gradually increased to 5.3-fold that of the SP204-sLV group (FIG. 5K). The final average tumor weight in mice treated with SP204-sLV was 0.13 g. compared to 0.53 g in mice treated with sLV and 1.03 g in mice treated with PBS buffer (FIG. 5L). Significant changes in body weight were not observed in the SP204-sLV or sLV groups during the treatment period, while more necrotic/apoptotic areas and less blood vessels were detected in the SP204-sLV group than in the sLV group. Similar results were observed in studies using a different animal model with DU145-derived xenograts (FIGS. 5M, 5N). No group exhibited significant changes in body weight during the treatment period.

Therapeutic Potential of Combination Therapy in the Xenograft and Orthotopic Prostate Cancer Models The effect of non-targeting liposomal drugs and targeting liposomal drugs, either alone or in combination, were analyzed in a xenograft prostate cancer model. NOD-SCID mice bearing DU145-derived xenografts were injected i.v. with LD, sLV, SP204-LD, SP204-sLV, LD+sLV, SP204-LD+SP204-sLV, or an equal volume of PBS. Doxorubicin and vinorelbine were administered through tail vein injection at 1 mg/kg every 3.5 days for a total of eight doses. Treatment with LD or sLV modestly inhibited tumor growth, but combined treatment with LD and sLV resulted in a statistically significant suppression of tumor growth (FIG. 6A). Administration of both LD and sLV inhibited growth by 70% as compared to untreated controls. Treatment with either LD or sLV, however, inhibited tumor growth by 64% or 45%, respectively (FIG. 6A). Groups receiving SP204-targeting liposomal drugs exhibited enhanced tumor growth inhibition as compared to all groups receiving non-targeting liposomal drugs. Administration of both SP204-LD and SP204-sLV inhibited tumor growth by 85%, whereas treatment with SP204-LD or SP204-sLV inhibited tumor growth by 76% or 64%, respectively (FIG. 6A). Body weight was not affected by any treatment (FIG. 6B). Mice co-treated with SP204-LD and SP204-sLV displayed markedly improved survival as compared to other treated groups (FIGS. 6C and 6D). These results indicate that the therapeutic efficacy of combined SP204-LD and SP204-sLV treatment is superior to that of other tested formulations in a prostate cancer xenograft model.

Orthotopic tumor models are more relevant than xenograft models with respect to both host-tumor interactions and response to therapy. We investigated the antitumor potential of combined treatment with SP204-LD and SP204-sLV by intravenously injecting these drugs into an orthotopic model of human prostate cancer, and subsequently examining PC3-Luc tumors, which stably express firefly luciferase, by bioluminescence imaging. Prior to the first therapeutic injection, we observed that growing orthotopic tumors were mainly located in the pelvic cavity.

Mice were injected with vehicle (PBS), docetaxel (5 mg/kg), liposomal drugs, or targeting liposomal drugs (doxorubicin 1 mg/kg; vinorelbine 2 mg/kg). The level of bioluminescence in the tumors of SP204-LD and SP204-sLV-treated mice was lower than that of other therapeutic groups (FIGS. 6E and 6F). Body weight was not significantly different between different treatments (FIG. 6G). Combined treatment with SP204-LD and SP204-sLV enhanced the antitumor effect and extended the survival of the orthotopic model mice as compared to the other groups (FIGS. 6H and 6I). At the end of the study, the median survival times for PBS, FD and FV, LD and sLV, SP204-LD and SP204-sLV, and docetaxel were 36, 39, 65, 72, and 58 days, respectively. Survival analysis with a log-rank test was performed to reveal that SP204-LD and SP204-sLV treatment significantly extend animal survival as compared to other tested treatments.

The prostate cancer cell-targeting peptide SP204-mediated targeting liposomes markedly increase the therapeutic efficacy of doxorubicin and vinorelbine in mouse prostate cancer xenograft and orthotropic models through enhancing drug delivery to tumor tissues. SP204 has high affinity toward prostate cancer cells and can induce endocytosis. SP204-conjugated liposomal drugs were significantly more effective in suppressing tumor growth. SP204 recognized a tumor antigen expressed on many prostate cancer specimens. This suggests that SP204 has potential as a targeting ligand to enhance the therapeutic efficacy of anti-cancer drugs.

The SP204 peptide can recognize surgical specimens of prostate cancer and enhance tumor therapy in a xenograft model with PC3 and DU145. Both PC3 and DU145 are CRPC cell lines. Vinorelbine targets the microtubule apparatus of cells, and docetaxel is a standard chemotherapeutic agent for patients with CRPC. SP204-LD and SP204-sLV can suppress CRPC tumor growth. Combining SP204-mediated targeting liposomes with drugs of two different mechanisms of action, such as doxorubicin (topoisomerase inhibitor) and vinorelbine (mitotic spindle inhibitor), significantly inhibits tumor growth of CRPC. These results suggest that SP204-LD and SP204-sLV might be useful for treatment of CRPC.

Coupling targeting peptide SP204 to lipid-based liposomal drugs does not affect the particle size or pharmacokinetics of drugs. The pharmacokinetic properties of SP204 peptide-conjugated targeting liposomes are identical to those of non-targeting liposomes. SP204-mediated targeting liposomes enhanced anticancer drug accumulation in tumor tissue without increasing drug delivery to non-cancerous host tissue or enhancing host toxicity.

SP204-SPION strongly and selectively accumulates in tumor tissues, suggesting it has great potential for use in prostate cancer-targeted imaging. Cancer stem cells (CSCs) play an important role in drug resistance development in prostate cancer. CD133, a member of the transmembrane glycoprotein family, is as an important marker for CSCs. PC204 has strong affinity for CD133' and CD133 PC3 cells, while the control phage demonstrated no binding activity to the tested cells (FIG. 8A). We cultured cancer cells attached to the tumorsphere, and observed strong responses by AP staining (FIG. 8B). We observed a gradual increase of large amounts of SRB in PC3 tumorspheres treated with SP204-LS, whereas very low doses of SRB were detectable in cells incubated with non-targeting LS (FIG. 8C). This indicates that the conjugation of liposome to SP204 enables effective internalization of SRB by PC3 tumorspheres.

Epithelial cell adhesion molecule (EpCAM) is over-expressed in many cancers including prostate cancer. It plays roles in cell-cell adhesion, invasion, migration, and proliferation. Over-expression of EpCAM leads to progression to advanced tumor stages and shorter recurrence-free survival. Double staining showed that nearly 90% of the EpCAM$^+$ PC3 cells were localized in PC204 (FIG. 8D). SP204 targets to prostate cancer cells and prostate cancer stem cells with high specificity. Therefore, SP204 has a high clinical potential for the treatment and molecular imaging of prostate cancer.

In conclusion, the invention relates to a novel peptide, SP204, capable of binding specifically to the cell surface of prostate cancer cells both in vitro and in vivo. Linking SP204 to liposomes containing doxorubicin and vinorelbine increased the therapeutic efficacy of these drugs in mice bearing human prostate cancer xenografts through enhanced tumor apoptosis and decreased tumor angiogenesis. The targeting peptide of the invention increased anti-cancer drug such as doxorubicin concentrations in tumor tissue targeted by the liposome, highlighting the enhancement of both delivery and penetration of doxorubicin into the tumor. The results suggest that the SP204 peptide is useful for specific targeting of tumor cells to treat prostate cancer, and to facilitate the molecular imaging of this malignancy.

What is claimed is:

1. A conjugate comprising:
   (a) an isolated or a synthetic targeting peptide comprising an amino add sequence that is at least 90% identical to SEQ ID NO: 8; and
   (b) a component, to which the targeting peptide is conjugated, the component being selected from the group consisting of polymeric micelles, lipoprotein-based drug carriers, nanoparticle drug carriers, a chemotherapeutic agent, a micelle, a liposome, dendrimers, a polymer, a lipid, an oligonucleotide, a peptide, a polypeptide, a protein, a prostate cancer cell, a stem cell, and an imaging agent,
   wherein the component is not an M13 phage.

2. The conjugate of claim 1, wherein the targeting peptide is conjugated to:
   (a) the chemotherapeutic agent;
   (b) the oligonucleotide;
   (c) the imaging agent; or
   (d) the liposome.

3. The conjugate claim 2, wherein the component is a PEGylated liposome.

4. The conjugate of claim 2, wherein the imaging agent is selected from the group consisting of quantum dots, superparamagnetic iron oxide nanoparticles, and a fluorescent dye encapsulated within a liposome.

5. The conjugate of claim 1, wherein the component is the liposome, and the conjugate further comprises one or more anti-cancer agents encapsulated within the liposome.

6. The conjugate claim 5, wherein the component is a PEGylated liposome.

7. The conjugate of claim 1, wherein the targeting peptide consists of less than 20 amino acid residues in length.

8. The conjugate claim 7, wherein the component is a PEGylated liposome.

9. The conjugate of claim 1, wherein the component is a PEGylated liposome.

10. The conjugate of claim 1, wherein the component is the imaging agent that is selected from the group consisting of quantum dots, superparamagnetic iron oxide nanoparticles, and a fluorescent dye encapsulated within a liposome.

11. A method for imaging and detecting the presence of prostate cancer cells in vivo or in vitro, comprising:
   (a) providing the conjugate of claim 10;
   (b) causing the prostate cancer cells to be exposed to the conjugate in vitro or in vivo,
   (c) allowing the targeting peptide of the conjugate to bind to the prostate cancer cells in vitro or in vivo; and
   (d) performing imaging to detect the presence of the prostate cancer cells in vitro or in vivo.

12. A kit comprising:
   (a) the conjugate of claim 10; and
   (b) a written instruction for use of the kit in imaging and detecting the presence of prostate cancer cells in vivo or in vitro.

13. An isolated or a synthetic targeting peptide comprising an amino acid sequence that is at least 90% identical to SEQ ID NO: 8 and that is conjugated to a component selected from the group consisting of a liposome, a PEGylated liposome, a nanoparticle, or an imaging agent, wherein the component is not an M13 phage.

14. The targeting peptide of claim 13, comprising the amino acid sequence of SEQ ID NO: 8.

15. The targeting peptide of claim 13, consisting of less than 20 amino acid residues in length.

16. The conjugate of claim 13, wherein the imaging agent is selected from the group consisting of quantum dots, superparamagnetic iron oxide nanoparticles, and a fluorescent dye encapsulated within a liposome.

17. A composition comprising:
   (a) liposomes;
   (b) a therapeutically effective amount of one or more chemotherapeutic agents, encapsulated within the liposomes; and
   (c) an isolated or a synthetic targeting peptide comprising an amino acid sequence that is at least 90% identical to SEQ ID NO: 8, being conjugated to the surfaces of the liposomes.

18. The composition of claim 17, comprising two or more different chemotherapeutic agents with each chemotherapeutic agent being separately encapsulated within the liposomes.

19. A method for treating prostate cancer, inhibiting prostate cancer cell growth, inducing prostate cancer cell cytotoxicity, and/or increasing the survival rate in a prostate cancer patient, comprising:
   administering an effective amount of the composition of claim 17 to the prostate cancer patient.

\* \* \* \* \*

```
                        SEQUENCE LISTING

<160> NUMBER OF SEQ ID NOS: 9

<210> SEQ ID NO 1
<211> LENGTH: 12
<212> TYPE: PRT
<213> ORGANISM: Artificial Sequence
<220> FEATURE:
<223> OTHER INFORMATION: phage clone No. SP103 displayed peptide
      sequence

<400> SEQUENCE: 1

Phe Pro Trp Thr Glu Pro Ser Tyr Lys Gln Gly Asp
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Phage clone No. SP108 displayed peptide
      sequence

<400> SEQUENCE: 2

Phe Pro Trp Thr Glu Pro Leu Tyr Lys Tyr Gly Glu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Phage clone No. SP135 displayed peptide
      sequence

<400> SEQUENCE: 3

Phe Pro Trp Thr Glu Pro Ser Tyr Lys Tyr Gly Asp
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Phage clone No. SP149 displayed peptide
```

-continued sequence

<400> SEQUENCE: 4

Met Pro Trp Lys Glu Ser Ala Trp Leu Glu Lys Ile
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Phage clone No. 150 displayed peptide sequence

<400> SEQUENCE: 5

Met Pro Trp Thr Glu Pro Asn Tyr Leu Leu Thr Gln
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Phage clone No. 195 displayed peptide sequence

<400> SEQUENCE: 6

Ile Pro Trp Lys Glu Ser Ala Cys Leu Ala Lys Ile
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Phage clone No. 196 displayed peptide sequence

<400> SEQUENCE: 7

Ala Pro Trp Leu Glu Gly Ser Tyr Lys Thr Val Tyr
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Phage clone No. 204 displayed peptide sequence

<400> SEQUENCE: 8

Lys Gln Phe Ser Ala Leu Pro Phe Asn Phe Tyr Thr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Phage clone No. 215 displayed peptide sequence

<400> SEQUENCE: 9

Ser Glu Phe Pro Arg Ser Trp Asp Met Glu Thr Asn
1               5                   10